United States Patent
Yamamoto et al.

(10) Patent No.: US 12,338,475 B2
(45) Date of Patent: Jun. 24, 2025

(54) METHOD FOR PRODUCING FUNCTIONAL SUBSTANCE

(71) Applicant: DAICEL CORPORATION, Osaka (JP)

(72) Inventors: Yuhei Yamamoto, Tokyo (JP); Hiroaki Yamamoto, Tokyo (JP)

(73) Assignee: Daicel Corporation, Osaka (JP)

( * ) Notice: Subject to any disclaimer, the term of this patent is extended or adjusted under 35 U.S.C. 154(b) by 320 days.

(21) Appl. No.: 17/153,702

(22) Filed: Jan. 20, 2021

(65) Prior Publication Data

US 2021/0222206 A1 Jul. 22, 2021

Related U.S. Application Data

(60) Provisional application No. 62/964,005, filed on Jan. 21, 2020.

(51) Int. Cl.
| | |
|---|---|
| *C12P 3/00* | (2006.01) |
| *A23L 33/135* | (2016.01) |
| *C12N 1/20* | (2006.01) |
| *C12R 1/145* | (2006.01) |

(52) U.S. Cl.
CPC .............. *C12P 3/00* (2013.01); *A23L 33/135* (2016.08); *C12N 1/20* (2013.01); *C12N 1/205* (2021.05); *C12R 2001/145* (2021.05)

(58) Field of Classification Search
CPC .. C12P 3/00; C12N 1/20; C12N 1/205; C12R 2001/145; A23L 33/135
See application file for complete search history.

(56) References Cited

U.S. PATENT DOCUMENTS 8,048,913 B2 * 11/2011 Setchell ............... A61K 31/352
549/399
2019/0323045 A1 10/2019 Masatake et al.

FOREIGN PATENT DOCUMENTS

| JP | H10-084984 A | 4/1998 |
|---|---|---|
| JP | 2011-160673 A | 8/2011 |
| JP | 2012-213378 A | 11/2012 |
| JP | 2013-192547 A | 9/2013 |
| JP | 2014-054234 A | 3/2014 |
| WO | WO 2012/033150 A1 | 3/2012 |
| WO | WO 2018/124135 A1 | 7/2018 |

OTHER PUBLICATIONS

Miller et al. "Bioconversion of Cellulose to Acetate with Pure Cultures of Ruminococcus albus and a Hydrogen-Using Acetogen", Applied and Environmental Microbiology, 1995, vol. 61, No. 11, pp. 3832-3835. (Year: 1995).*
Miller et al. "Fermentations by saccharolytic intestinal bacteria", The American Journal of Clinical Nutrition, 1979, vol. 32, Issue 1, pp. 164-172. (Year: 1979).*
Setchell et al. "Equol: History, Chemistry, and Formation", The Journal of Nutrition, 2010, vol. 140, pp. 1355S-1362S. (Year: 2010).*
Mayo (Nutrients 2019, 11, 2231) (Year: 2019).*
Mohan et al. "*Clostridium asparagiforme* sp. nov., isolated from the human faecal sample", Systematic and Applied Microbiology, 2006, vol. 29, Issue 4, pp. 292-299. (Year: 2006).*
Hur et al. "Isolation of human intestinal bacteria metabolizing the natural isoflavone glycosides daidzin and genistin", Archives of Microbiology, 2000, vol. 174, pp. 422-428. (Year: 2000).*
Decroos et al. "Isolation and characterisation of an equol-producing mixed microbial culture from a human faecal sample and its activity under gastrointestinal conditions", Archives of Microbiology, 2005, vol. 183, pp. 45-55. (Year: 2005).*
Miller et al., "Bioconversion of cellulose to acetate with pure cultures of Ruminococcus albus and aa hydrogen-using acetogen", Applied and Environmental Microbiology, 1995, vol. 61, No. 11, pp. 3832-3835.
Haas and Blanchard, Int J Syst Evol Microbiol, 2019, 70.
Decroos, Karel et al., "Isolation and characterisation of an equol-producing mixed microbial culture from a human faecal sample and its activity under gastrointestinal conditions" Arch Microbio, 2005, pp. 45-55, vol. 183.
Minamida, Kimiko et al., "Production of Equol from Daidzein by Gram-Positive Rod-Shaped Bacterium Isolated from Rat Intestine" Journal of Bioscience and Bioengineering, 2006, pp. 247-250, vol. 102, No. 3.

* cited by examiner

*Primary Examiner* — Abigail Vanhorn
*Assistant Examiner* — Deepa Mishra
(74) *Attorney, Agent, or Firm* — Knobbe, Martens, Olson & Bear, LLP

(57) ABSTRACT

An object of the present invention is to a method for producing a functional substance utilizing a reaction requiring hydrogen, which production method is safe and efficient; and this object is achieved by a method for producing a functional substance utilizing a reaction requiring hydrogen, the method comprising: supplying the hydrogen by culturing of a hydrogen-producing microorganism.

8 Claims, No Drawings

METHOD FOR PRODUCING FUNCTIONAL SUBSTANCE

CROSS-REFERENCE TO RELATED PATENT APPLICATIONS

This application claims priority U.S. Provisional Application No. 62/964,005, filed Jan. 21, 2020, which is incorporated by reference in its entirety.

TECHNICAL FIELD

The present invention relates to a method for producing a functional substance utilizing a reaction requiring hydrogen.

BACKGROUND ART

Production processes of functional substances such as equol compounds and urolithin compounds often include a reaction requiring hydrogen. For example, some bioconversion reactions utilizing biological materials such as microorganisms, cells other than microorganism cells, or enzymes derived from organisms require hydrogen, or are activated by hydrogen. For example, it is known that reactions requiring hydrogen often occur when food components are metabolized by intestinal bacteria in the intestine to produce functional metabolites.

Known examples of bioconversion reactions requiring hydrogen include a reaction that produces an equol compound from isoflavone, a reaction that produces a urolithin compound from ellagitannin or ellagic acid, a reaction that produces 1-(3,5-dihydroxyphenyl)-3-(2,4,6-trihydroxyphenyl) propan-2-ol from epigallocatechin, and a reaction that produces lunularin from trans-resveratrol. In general, hydrogen is required for dehydroxylation reaction. For industrially carrying out such a bioconversion reaction requiring hydrogen to enable industrial production of a functional substance, supply of hydrogen to the bioconversion reaction system, for example, fermentation, from outside the system has been conventionally necessary. For example, a method in which a gas phase is replaced with hydrogen gas before fermentation, or a method in which hydrogen is supplied during culture has been employed (Patent Document 1).

Further, in industrial production of a functional substance utilizing a fermenter, when hydrogen is supplied from outside, stirring is required for uniformly supplying the hydrogen into the system. This has often caused damaging of the microorganism that produces the functional substance, foaming, or the like.

On the other hand, hydrogen production methods using microorganisms have been reported. For example, a method for producing hydrogen and butanol from a cellulose substrate by mixed culture of bacteria belonging to the genus *Clostridium* is known (Patent Document 2).

Further, a method for producing hydrogen gas by culturing of at least one bacterium selected from bacteria belonging to the genus *Escherichia*, bacteria belonging to the genus *Enterobacter*, bacteria belonging to the genus *Saccharomyces*, bacteria belonging to the genus *Thermotoga*, bacteria belonging to the genus *Clostridium*, and bacteria belonging to the genus *Corynebacterium* in a culture medium containing a carbohydrate and a nitrogen source is known (Patent Document 3).

Further, a method in which the *Rhodopseudomonas palustris* R-1 strain (FERM P-15615) is cultured, and the resulting culture is added to an anaerobically treated waste sugar liquid containing acetic acid, ethanol, and the like, followed by irradiating the resulting mixture with light to produce hydrogen is known (Patent Document 4).

CITATION LIST

Patent Document

Patent Document 1: JP 2014-054234 A
Patent Document 2: JP 2012-213378 A
Patent Document 3: JP 2011-160673 A
Patent Document 4: JP H10-084984 A

SUMMARY OF INVENTION

Technical Problem

An object of the present invention is to provide a method for producing a functional substance utilizing a reaction requiring hydrogen, which production method is safe and efficient.

Solution to Problem

As a result of intensive study, the present inventors discovered that, in the reaction requiring hydrogen, the above problem can be solved by supplying the hydrogen by culture of a hydrogen-producing microorganism, thereby completing the present invention.

The present invention is as described below.

<1> A method for producing a functional substance utilizing a reaction requiring hydrogen, the method comprising:
supplying the hydrogen by culturing of a hydrogen-producing microorganism.

<2> The method according to <1>, wherein the reaction requiring hydrogen is a bioconversion reaction.

<3> The method according to <1> or <2>, wherein the functional substance is a functional metabolite produced by metabolism in an intestinal bacterium.

<4> The method according to <3>, wherein the metabolism in the intestinal bacterium is a dehydroxylation reaction.

<5> The method according to <3> or <4>, wherein the functional metabolite is an equol compound.

<6> The method according to <3> or <4>, wherein the functional metabolite is a urolithin compound.

<7> The method according to <5>, wherein the equol compound is equol or 5-hydroxyequol.

<8> The method according to <6>, wherein the urolithin compound is urolithin A, urolithin B, urolithin C, urolithin D, urolithin E, urolithin M3, urolithin M4, urolithin M5, urolithin M6, isourolithin A, or 6H-dibenzo[b,d]pyran-6-one.

The method according to any one of <1> to <8, wherein the hydrogen-producing microorganism is one or more bacteria selected from the group consisting of bacteria belonging to the genus *Clostridium*, bacteria belonging to the genus *Enterobacter*, bacteria belonging to the genus *Rhodopseudomonas*, bacteria belonging to the genus *Achromobacter*, bacteria belonging to the genus *Arthrobacter*, bacteria belonging to the genus *Serratia*, bacteria belonging to the genus *Alcaligenes*, bacteria belonging to the genus *Ruminococcus*, bacteria belonging to the genus *Blautia*, and bacteria belonging to the genus *Sarcina*.

<10> The method according to any one of <1> to <9>, wherein the hydrogen-producing microorganism is one or more bacteria selected from the group consisting of bacteria belonging to *Clostridium asparagiforme*, bacteria belonging to *Clostridium bolteae*, bacteria belonging to *Clostridium butyricum*, bacteria belonging to *Clostridium citroniae*, bacteria belonging to *Enterobater aerogenes*, bacteria belonging to *Blautia producta*, bacteria belonging to *Blautia coccoides*, bacteria belonging to *Blautia schinkii*, and bacteria belonging to *Rhodopseudomonas palustris*.

<11> The method according to any one of <1> to <10>, wherein, in the hydrogen-supplying step, the hydrogen-producing microorganism coexists with a microorganism which produces the functional substance.

<12> The method according to <11>, wherein the microorganism which produces the functional substance does not substantially produce hydrogen.

<13> The method according to any one of <1> to <12>, wherein, in the hydrogen-supplying step,
the microorganism which produces the functional substance from a precursor of the functional substance is the hydrogen-producing microorganism; and
a microorganism which produces the precursor is a microorganism which produces the precursor from a raw material of the precursor using hydrogen supplied by the hydrogen-producing microorganism.

<14> The method according to <13>, wherein the microorganism which produces the precursor is a microorganism which does not substantially produce hydrogen.

<15> A method for producing a functional food, the method comprising:
producing a functional substance utilizing a reaction requiring hydrogen, the hydrogen being supplied by culturing of a hydrogen-producing microorganism; and
mixing the functional substance with a raw material of a food.

<16> A method for producing a food additive, the method comprising:
producing a functional substance utilizing a reaction requiring hydrogen, the hydrogen being supplied by culturing of a hydrogen-producing microorganism; and
mixing the functional substance with a raw material of a food additive.

<17> A method for producing a cosmetic product, the method comprising:
producing a functional substance utilizing a reaction requiring hydrogen, the hydrogen being supplied by culturing of a hydrogen-producing microorganism; and
mixing the functional substance with a raw material of a cosmetic product.

<18> A method for producing a pharmaceutical, the method comprising:
producing a functional substance utilizing a reaction requiring hydrogen, the hydrogen being supplied by culturing of a hydrogen-producing microorganism; and
mixing the functional substance with a raw material of a pharmaceutical.

<19> A method for producing a quasi-drug, the method comprising:
producing a functional substance utilizing a reaction requiring hydrogen, the hydrogen being supplied by culturing of a hydrogen-producing microorganism; and
mixing the functional substance with a raw material of a quasi-drug.

Advantageous Effects of Invention

According to the present invention, problems in the conventional methods of producing a functional substance, more specifically, low solubility of hydrogen in a solution, and problems in safety and laboriousness during handling of hydrogen, can be solved to provide a safe and efficient method for producing a functional substance.

Further, in cases where the microorganism that produces the functional substance is an anaerobic microorganism, even when the culture liquid contains a small amount of oxygen, the hydrogen-producing microorganism consumes the oxygen to provide an environment that readily allows the growth of the microorganism that produces the functional substance. Further, the oxidation-reduction potential (ORP) of the culture liquid can be adjusted to a potential suitable for the production of the functional substance.

Moreover, in the means of the present invention, wherein hydrogen is supplied by a hydrogen-producing microorganism in the system, the stirring rate only needs to be as high as a rate at which the hydrogen-producing microorganism can be uniformly distributed. Thus, since the stirring rate can be suppressed compared to the conventional methods, damaging of the microorganism that produces the functional substance, and foaming, during the culture can be prevented.

DESCRIPTION OF EMBODIMENTS

The present invention is described below in detail.

The present invention is a method for producing a functional substance utilizing a reaction requiring hydrogen, the method comprising the step of supplying the hydrogen by culturing of a hydrogen-producing microorganism.

The method for producing a functional substance according to the present invention utilizes a reaction requiring hydrogen. As long as the reaction requiring hydrogen is a reaction in the process of producing a functional substance, the product after the reaction may be any of the functional substance, a raw material of the functional substance, and an intermediate product such as a precursor of the functional substance. The reaction also includes those in cases where hydrogen is utilized for activation of the reaction, such as cases where hydrogen acts as an electron donor in an enzymatic reaction.

The reaction requiring hydrogen includes reactions in which a reactant is converted to a product utilizing an inorganic material or the like. The reaction, however, is preferably the so-called bioconversion reaction, in which a reactant is converted to a product utilizing a biological material such as a microorganism, cells other than microorganism cells, or an enzyme derived from an organism.

The functional substance in the present invention is, for example, a substance involved in a biological regulatory function of a mammal such as human. Examples of the functional substance include substances that are conceptually the same as effective components of foods and food additives, cosmetic products, pharmaceuticals, quasi-drugs, and the like. The functional substance may also be referred to as functional component or the like. The functional substance in the present invention is preferably a functional metabolite produced by metabolism in an intestinal bacterium. The metabolism in the intestinal bacterium is preferably a dehydroxylation reaction. The metabolism in the intestinal bacterium is also preferably a dehydroxylation reaction by the intestinal bacterium. The dehydroxylation reaction means a reaction in which a hydroxyl group is eliminated from a substrate containing the hydroxyl group. Examples of the functional metabolite include equol compounds, urolithin compounds, and lunularin compounds.

The functional substance in the present invention may also be a functional substance whose raw material or precursor is a functional substance.

The equol compound in the present invention is represented by the following General Formula (1):

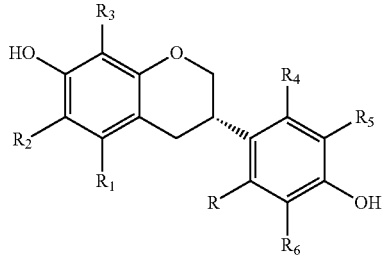

(1)

(wherein $R_1$ to $R_7$ each represent a hydroxyl group or hydrogen atom).

Specific examples of the equol compound include any compound included in the compounds represented by the General Formula (1), including equol (which is also called 4',7-isoflavandiol) and 5-hydroxyequol.

The urolithin compound in the present invention is represented by the following General Formula (2):

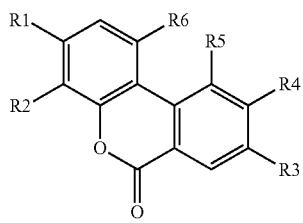

(2)

(wherein $R_1$ to $R_6$ each represent a hydroxyl group, hydrogen atom, or methoxy group, with the proviso that one or more of $R_1$ to $R_6$ represents a hydroxyl group).

Specific examples of the urolithin compound include any compound included in the compounds represented by the General Formula (2), including urolithin A, urolithin B, urolithin C, urolithin D, urolithin E, urolithin M3, urolithin M4, urolithin M5, urolithin M6, isourolithin A, and 6H-dibenzo[b,d]pyran-6-one.

The lunularin compound in the present invention is a general term for the compounds represented by the following General Formula (3) and the compounds represented by the following General Formula (4):

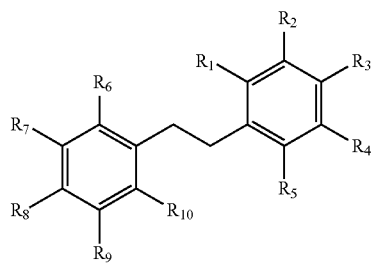

(3)

(wherein $R_1$ to $R_{10}$ each represent a hydroxyl group or hydrogen atom);

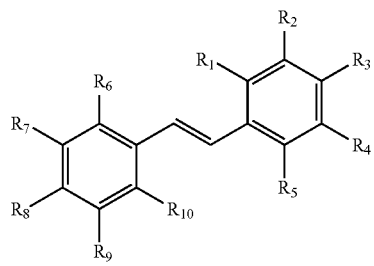

(4)

(wherein $R_1$ to $R_{10}$ each represent a hydroxyl group or hydrogen atom).

Specific examples of the compound represented by the General Formula (3) include any compound included in the compounds represented by the General Formula (3), including dihydroresveratrol, which is represented by the following Formula (5):

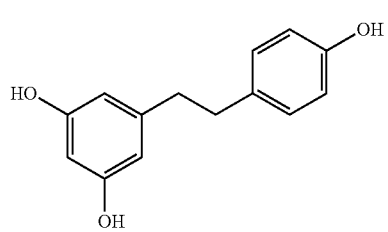

(5)

Specific examples of the compound represented by the General Formula (4) include any compound included in the compounds represented by the General Formula (4), including 3,4'-dihydroxy-trans-stilbene, which is represented by the following Formula (6):

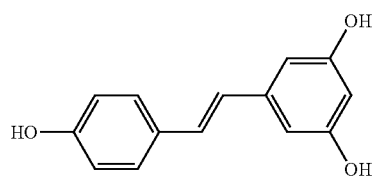

(6)

The term "compound" as used in the present description is merely a formal expression for the purpose of classification. For example, "urolithin compound" is a concept including smaller groups included in the "urolithin compound", such as urolithin A and urolithin B. "Urolithin compound" may also be simply referred to as "urolithin".

The hydrogen is supplied by culture of a hydrogen-producing microorganism.

The hydrogen-producing microorganism is not limited as long as it is a microorganism capable of producing hydrogen by culture. The genus, species, and strain of the microorganism are not limited, and one or more bacteria may be used.

Examples of the hydrogen-producing microorganism include bacteria belonging to the genus *Clostridium*, bacteria belonging to the genus *Enterobacter*, bacteria belonging to the genus *Rhodopseudomonas*, bacteria belonging to the genus *Achromobacter*, bacteria belonging to the genus *Arthrobacter*, bacteria belonging to the genus *Serratia*, bacteria belonging to the genus *Alcaligenes*, bacteria belonging to the genus *Ruminococcus*, bacteria belonging to the genus *Sarcina*, and bacteria belonging to the genus *Blautia*.

Preferred examples of the hydrogen-producing microorganism include bacteria belonging to *Clostridium asparagiforme*, bacteria belonging to *Clostridium bolteae*, bacteria belonging to *Clostridium butyricum*, bacteria belonging to *Clostridium citroniae*, bacteria belonging to *Enterobater aerogenes*, bacteria belonging to *Rhodopseudomonas palustris*, bacteria belonging to *Blautia producta*, bacteria belonging to *Blautia coccoides*, and bacteria belonging to *Blautia schinkii*.

More preferred examples of the hydrogen-producing microorganism include the *Clostridium asparagiforme* DSM 15981 strain, the *Clostridium bolteae* JCM 12243 strain, and the *Clostridium citroniae* DSM 19261 strain.

In the present description, the accession numbers of microbial strains beginning with the letters "DSM" are numbers given to microorganisms stored in DSMZ (Deutsche Sammlung von Mikroorganismen und Zellkulturen GmbH).

In the present description, the accession numbers of microbial strains beginning with the letters "JCM" are numbers given to microorganisms stored in Japan Collection of Microorganisms (Microbe Division, RIKEN BioResource Center; 3-1-1 Koyadai, Tsukuba, Ibaraki 305-0074, Japan).

Microbial strains that are substantially the same as any of the above-deposited strains may also be used. Substantially the same microbial strain means a microorganism which is capable of producing hydrogen by culture, and whose base sequence of the 16S rRNA gene has a homology of not less than 97.5%, preferably not less than 98%, more preferably 99%, to the base sequence of the 16S rRNA gene of the above microbial strain. Substantially the same microbial strain may also be a microbial strain prepared by mutagenesis, genetic recombination, selection of a natural mutant strain, or the like from the above microbial strain, or from a microbial strain that is substantially the same as the above microbial strain.

In the hydrogen-supplying step, the hydrogen-producing microorganism preferably coexists with a microorganism that produces the functional substance.

Examples of the microorganism which produces the functional substance include bacteria belonging to *Adlercreutzia equolifaciens*, bacteria belonging to *Asaccharobacter celatus*, bacteria belonging to *Bacteroides ovatus*, bacteria belonging to *Bacteroides plebeius*, bacteria belonging to *Bacteroides vulgatus*, bacteria belonging to *Bifidobacterium animalis*, bacteria belonging to *Bifidobacterium bifidum*, bacteria belonging to *Bifidobacterium infantis*, bacteria belonging to *Bifidobacterium longum*, bacteria belonging to *Bifidobacterium pseudolongum*, bacteria belonging to *Bifidobacterium breve*, bacteria belonging to *Citrobacter murliniae*, bacteria belonging to *Clostridium asparagiforme*, bacteria belonging to *Clostridium bolteae*, bacteria belonging to *Clostridium citroniae*, bacteria belonging to *Clostridium scindens*, bacteria belonging to *Coriobacteriaceae* sp., bacteria belonging to *Eggerthella* sp., bacteria belonging to *Eggerthella lenta*, bacteria belonging to *Enterococcus faecium*, bacteria belonging to *Eubacterium* sp., bacteria belonging to *Finegoldia magna*, bacteria belonging to *Gordonibacter pamelaeae*, bacteria belonging to *Gordonibacter urolithinfaciens*, bacteria belonging to *Gordonibacter faecihominis*, bacteria belonging to *Lactobacillus plantarum*, bacteria belonging to *Lactobacillus fermentum*, bacteria belonging to *Lactobacillus rhamnosus*, bacteria belonging to *Lactococcus garvieae*, bacteria belonging to *Paraeggerthella* sp., bacteria belonging to *Peptoniphilus harei*, bacteria belonging to *Ruminococcus productus*, bacteria belonging to *Slackia equolifaciens*, bacteria belonging to *Slackia isoflavoniconvertens*, bacteria belonging to *Slackia* sp., bacteria belonging to *Streptococcus intermedius*, and bacteria belonging to *Streptococcus constellatus*.

In this case, the microorganism which produces the functional substance may also be a microorganism which does not substantially produce hydrogen. The term "does not substantially produce hydrogen" means that the microorganism does not produce the functional substance in an environment in which neither the hydrogen supplied by the hydrogen-producing microorganism nor hydrogen supplied separately is present.

Specific examples of the microorganism which produces the functional substance, but which does not substantially produce hydrogen include bacteria belonging to *Adlercreutzia equolifaciens*, bacteria belonging to *Asaccharobacter celatus*, bacteria belonging to *Bifidobacterium animalis*, bacteria belonging to *Bifidobacterium bifidum*, bacteria belonging to *Bifidobacterium infantis*, bacteria belonging to *Bifidobacterium longum*, bacteria belonging to *Bifidobacterium pseudolongum*, bacteria belonging to *Bifidobacterium breve*, bacteria belonging to *Citrobacter murliniae*, bacteria belonging to *Eggerthella* sp., bacteria belonging to *Eggerthella lenta*, bacteria belonging to *Finegoldia magna*, bacteria belonging to *Gordonibacter pamelaeae*, bacteria belonging to *Gordonibacter urolithinfaciens*, bacteria belonging to *Gordonibacter faecihominis*, bacteria belonging to *Lactobacillus plantarum*, bacteria belonging to *Lactobacillus fermentum*, bacteria belonging to *Lactobacillus rhamnosus*, bacteria belonging to *Lactococcus garvieae*, bacteria belonging to *Paraeggerthella* sp., bacteria belonging to *Peptoniphilus harei*, bacteria belonging to *Slackia equolifaciens*, bacteria belonging to *Slackia isoflavoniconvertens*, bacteria belonging to *Slackia* sp., bacteria belonging to *Streptococcus intermedius*, and bacteria belonging to *Streptococcus constellatus*.

For example, in cases where the functional substance is equol, and its raw material is daidzein, examples of the microorganism which produces equol include bacteria belonging to *Asaccharobacter celatus*, more specifically, for example, the *Asaccharobacter celatus* DSM 18785 strain. This microbial strain is a microbial strain that does not substantially produce hydrogen.

In cases where the functional substance is urolithin C, and its raw material is ellagic acid, examples of the microorganism which produces urolithin C include bacteria belonging to *Gordonibacter pamelaeae*. These bacteria preferably do not substantially produce hydrogen.

In the hydrogen-supplying step, the hydrogen-producing microorganism is also preferably a microorganism that produces the functional substance.

For example, in cases where the functional substance is urolithin A, and its raw material is urolithin C, the microorganism which produces urolithin A from urolithin C may be a hydrogen-producing microorganism such as a bacterium belonging to the genus *Clostridium*.

In another preferred mode, in the hydrogen-supplying step, the microorganism which produces the functional substance (second functional substance) using a precursor of the functional substance (first functional substance) as a raw material is the hydrogen-producing microorganism, and the microorganism which produces the precursor produces the precursor from a raw material of the precursor using hydrogen supplied by the hydrogen-producing microorganism. In this mode, the microorganism that produces the precursor is more preferably a microorganism that does not substantially produce hydrogen. The first functional substance itself may also be the functional substance.

For example, in one mode, the microorganism which produces urolithin A (functional substance) using urolithin C (precursor of the functional substance) as a raw material is the hydrogen-producing microorganism, and the microorganism which produces urolithin C is a microorganism which uses hydrogen supplied by the hydrogen-producing microorganism to produce the urolithin C from ellagic acid. In this case, examples of the microorganism that produces urolithin C include bacteria belonging to *Gordonibacter pamelaeae*. These bacteria preferably do not substantially produce hydrogen. Examples of the microorganism that produces urolithin A include bacteria belonging to the genus *Clostridium*, which are hydrogen-producing microorganisms at the same time.

In another preferred mode, the microorganism that produces the precursor of the functional substance (first functional substance) from the raw material is the hydrogen-producing microorganism, and the microorganism that produces the functional substance (second functional substance) produces the functional substance from the precursor using hydrogen supplied by the hydrogen-producing microorganism. In this mode, the microorganism that produces the functional substance is more preferably a microorganism that does not substantially produce hydrogen. As long as the desired final product can be produced from the starting material, the first, the second, and later functional substances, and the first, the second, and later microorganisms may be contained in the system, and each of the hydrogen-producing microorganism and the microorganism which does not substantially produce hydrogen may be a microorganism for any of the reaction stages.

The culture conditions for the hydrogen-producing microorganism may be culture conditions that are normally used for culture of the microorganism, or culture conditions provided by appropriately modifying those culture conditions, as long as the hydrogen-producing microorganism can produce hydrogen. In one mode, for example, a precursor of hydrogen such as formic acid is added to the medium.

The culture medium (medium) is not limited, and examples thereof include ANAEROBE BASAL BROTH (ABB medium), manufactured by Oxoid Limited; Wilkins-Chalgren Anaerobe Broth (CM0643), manufactured by Oxoid Limited; and GAM medium and modified GAM medium, manufactured by Nissui Pharmaceutical Co., Ltd.

A water-soluble organic matter may also be added to the medium as a carbon source. Examples of the water-soluble organic matter include the following compounds: sugars such as glucose, arabinose, sorbitol, fructose, mannose, sucrose, trehalose, and xylose; alcohols such as glycerol; organic acids such as valeric acid, butyric acid, propionic acid, acetic acid, formic acid, fumaric acid, and succinic acid; and polysaccharides such as dextrin.

The concentration of the organic matter added to the medium as a carbon source may be appropriately adjusted such that efficient growth is possible. In general, the amount of the organic matter added may be selected within the range of not more than 80 wt %, preferably not more than 50 wt %, more preferably not more than 25 wt %.

In addition to the carbon source, a nitrogen source may be added to the medium. As the nitrogen source, various nitrogen compounds applicable to ordinary fermentation may be used. Examples of preferred inorganic nitrogen sources include ammonium salts and nitrates, more preferably, ammonium sulfate, ammonium chloride, ammonium phosphate, ammonium hydrogen phosphate, potassium nitrate, and sodium nitrate.

Examples of organic nitrogen sources include amino acids such as glutamic acid, arginine, and ornithine; fats and oils such as oleic acid; yeast extracts; milk peptone; soy peptone; meat extracts (such as Ehrlich bonito extracts, Lab-Lemco powder, and fish and shellfish extracts), liver extracts, and digested serum powders.

Besides the carbon source and the nitrogen source, inorganic compounds, for example, cofactors such as vitamins, and various salts, may be added to the medium. By this, the growth and the activity can be enhanced in some cases. Examples of the growth-aiding factors for microorganisms, derived from animals and plants, include the following inorganic compounds and vitamins.

Inorganic compounds Vitamins
Potassium dihydrogen phosphate Biotin
Magnesium sulfate Folic acid
Manganese sulfate Pyridoxine
Sodium chloride Thiamine
Cobalt chloride Riboflavin
Calcium chloride Nicotinic acid
Zinc sulfate Pantothenic acid
Copper sulfate Vitamin B12
Alum Thioctic acid
Sodium molybdate p-Aminobenzoic acid
Potassium chloride
Boric acid and the like
Nickel chloride
Sodium tungstate
Sodium selenate
Ammonium ferrous sulfate
Sodium acetate trihydrate
Magnesium sulfate heptahydrate
Manganese sulfate tetrahydrate In cases where anaerobic culture is carried out, the growth can be improved in some cases by adding a reducing agent such as cysteine, cystine, sodium sulfate, sulfite, ascorbic acid, glutathione, thioglycolic acid, or rutin; or an enzyme that decomposes active oxygen species, such as catalase or superoxide dismutase, to the medium.

The gas phase and the aqueous phase during the culture preferably do not contain air or oxygen. For example, nitrogen and/or hydrogen is/are contained at an arbitrary ratio(s), or nitrogen and/or carbon dioxide is/are contained at an arbitrary ratio(s). These may be supplied in a gas state.

Separately from the hydrogen produced by the hydrogen-producing microorganism, hydrogen may be supplied to the culture liquid. In such a case, the hydrogen is supplied such that the ratio of hydrogen in the gas phase, including the hydrogen from the hydrogen-producing microorganism, is usually not less than 0.5%, preferably not less than 1.0%, more preferably not less than 2.0%, and such that, on the other hand, the ratio is usually not more than 100%, preferably not more than 20%, more preferably not more than 10%.

The method for supplying the gas is not limited, and may be, for example, a method in which the gas phase is replaced with the above gas before the culture, a method in which the above gas is supplied also during the culture from the bottom of the culture vessel, a method in which the gas is supplied to the gas phase portion of the culture vessel, or a method in which the aqueous phase is bubbled with the above gas before the culture.

The aeration rate is, for example, 0.05 to 2 vvm. An aeration rate of 0.01 to 0.5 vvm is preferred. The gas to be mixed may also be supplied as nanobubbles.

The culture temperature is preferably 20° C. to 45° C., more preferably 25° C. to 40° C., still more preferably 30° C. to 37° C.

The pressure condition of the culture vessel is not limited as long as the condition allows the growth. The pressure condition is, for example, within the range of 0.001 to 1 MPa, preferably 0.01 to 0.5 MPa.

The culture period is, for example, usually 8 to 340 hours, preferably 12 to 170 hours, more preferably 16 to 120 hours.

In cases where the culture is carried out using a hydrogen-producing microorganism without replacement of the gas phase with hydrogen, a lower stirring rate can be employed compared to cases of normal culture in which no hydrogen-producing microorganism is used, but in which the gas phase is replaced with hydrogen. Even the lower stirring rate enables achievement of a yield of the functional substance equivalent to the yield obtained in the cases in which no hydrogen-producing microorganism is used, but in which the gas phase is replaced with hydrogen. More specifically, the stirring rate is preferably not more than 500 rpm, more preferably not more than 400 rpm, still more preferably not more than 300 rpm, still more preferably not more than 200 rpm. The stirring rate is usually not less than 100 rpm.

Another aspect of the present invention is a method for producing a functional food. The food includes beverages.

The method for producing a functional food of the present aspect comprises the step of producing a functional substance utilizing a reaction requiring hydrogen, the hydrogen being supplied by culturing of a hydrogen-producing microorganism. Regarding details of the method, the description for the method for producing a functional substance is applied.

The method for producing a functional food of the present aspect also comprises the step of mixing the functional substance with a raw material of a food. The food is produced according to a conventional method by mixing an ordinary raw material of the food with the functional substance produced in the step described above, and the timing of the mixing is not limited. Examples of the raw material of the food include food additives. Further, if necessary, the food may be enclosed in an appropriate container such as a bottle, bag, can, box, or pack.

The food may contain, as a major component, water, protein, carbohydrate, lipid, vitamin, mineral, organic acid, organic base, juice, flavor, or the like.

Examples of the protein include animal and plant proteins such as whole milk powder, skimmed milk powder, semi-skimmed milk powder, casein, soy protein, chicken egg protein, and meat protein; hydrolysates thereof, and butter.

Examples of the carbohydrate include sugars, processed starches (dextrin, soluble starch, British starch, oxidized starch, starch ester, starch ether, and the like), and dietary fibers.

Examples of the lipid include lard; and vegetable oils and fats such as safflower oil, corn oil, rapeseed oil, and palm oil, and their fractionated oils, hydrogenated oils, and transesterified oils.

Examples of the vitamin include vitamin A, carotenes, vitamin Bs, vitamin C, vitamin Ds, vitamin E, vitamin Ks, vitamin P, vitamin Q, niacin, nicotinic acid, pantothenic acid, biotin, inositol, choline, and folic acid.

Examples of the mineral include calcium, potassium, magnesium, sodium, copper, iron, manganese, zinc, selenium, and whey minerals.

Examples of the organic acid include malic acid, citric acid, lactic acid, and tartaric acid.

Two or more of these components may be used in combination. These components may be synthetic products.

The content of the functional substance produced in the step described above with respect to the total amount of the food is not limited. The content is preferably a content with which a desired effect can be obtained from the functional substance when the food is ingested. The content of the functional substance with respect to the total amount of the food is dependent on the type and the desired effect of the functional substance, and may be selected within the range of usually 0.001 wt % to 80 wt %, preferably 0.01 wt % to 50 wt %, more preferably 0.1 wt % to 25 wt %.

In cases where the food is a supplement, it may be in any form such as a solid, gel-like product, or liquid product. Examples of the form include various processed foods, powders, tablets, balls, capsules, jellies, and granules. Further, if necessary, the supplement may be enclosed in an appropriate container such as a bottle, bag, can, box, or pack.

The supplement may contain an additive, and examples of the additive include excipients such as dextrin; preservatives such as vitamin C; corrigents such as vanillin; dyes such as safflower dye; monosaccharides, oligosaccharides, and polysaccharides (for example, glucose, fructose, sucrose, saccharose, and carbohydrates containing these); acidulants; perfumes; fats and oils; emulsifiers; whole milk powder; and agar. Two or more of these components may be used in combination. These components may be synthetic products.

Another aspect of the present invention is a method for producing a food additive. The food additive also includes food additives for beverages.

The method for producing a food additive of the present aspect comprises the step of producing a functional substance utilizing a reaction requiring hydrogen, the hydrogen being supplied by culturing of a hydrogen-producing microorganism. Regarding details of the method, the description for the method for producing a functional substance is applied.

The method for producing a food additive of the present aspect also comprises the step of mixing the functional substance with a raw material of a food additive. The food additive is produced according to a conventional method by mixing an ordinary raw material of the food additive with the functional substance produced in the step described above, and the timing of the mixing is not limited. Further, if necessary, the food additive may be enclosed in an appropriate container such as a bottle, bag, can, box, or pack.

Examples of the raw material of the food additive include coagulants, brine, activated carbon, sweeteners, coloring agents, perfumes, preservatives, antioxidants, and nutrient enrichment agents.

The content of the functional substance produced in the step described above with respect to the total amount of the food additive is not limited. The content is preferably a content with which a desired effect can be obtained from the functional substance when the food additive is ingested. The content of the functional substance with respect to the total amount of the food additive is dependent on the type and the desired effect of the functional substance, and may be selected within the range of usually 0.001 wt % to 80 wt %, preferably 0.01 wt % to 50 wt %, more preferably 0.1 wt % to 25 wt %.

Another aspect of the present invention is a method for producing a cosmetic product.

The method for producing a cosmetic product of the present aspect comprises the step of producing a functional substance utilizing a reaction requiring hydrogen, the hydrogen being supplied by culturing of a hydrogen-producing microorganism. Regarding details of the method, the description for the method for producing a functional substance is applied.

The method for producing a cosmetic product of the present aspect also comprises the step of mixing the functional substance with a raw material of a cosmetic product. The cosmetic product is produced according to a conventional method by mixing an ordinary raw material of the cosmetic product with the functional substance produced in the step described above, and the timing of the mixing is not limited. When necessary, the cosmetic product may be prepared into a desired formulation, for example, a liquid formulation such as an aqueous solution, lotion, spray liquid, suspension, or emulsion; a semisolid formulation such as a cream or paste; or a gel formulation. Further, if necessary, the cosmetic product may be enclosed in an appropriate container such as a bottle, bag, can, spray can, spray container, box, or pack.

The content of the functional substance produced in the step described above with respect to the total amount of the cosmetic product is not limited. The content is preferably a content with which a desired effect can be obtained from the functional substance when the cosmetic product is, for example, applied. The content of the functional substance with respect to the total amount of the cosmetic product is dependent on the type and the desired effect of the functional substance, and may be selected within the range of usually 0.001 wt % to 80 wt %, preferably 0.01 wt % to 50 wt %, more preferably 0.1 wt % to 25 wt %.

Another aspect of the present invention is a method for producing a pharmaceutical.

The method for producing a pharmaceutical of the present aspect comprises the step of producing a functional substance utilizing a reaction requiring hydrogen, the hydrogen being supplied by culturing of a hydrogen-producing microorganism. Regarding details of the method, the description for the method for producing a functional substance is applied.

The method for producing a pharmaceutical of the present aspect also comprises the step of mixing the functional substance with a raw material of a pharmaceutical. The pharmaceutical is produced according to a conventional method by mixing an ordinary raw material of the pharmaceutical with the functional substance produced in the step described above, and the timing of the mixing is not limited. The pharmaceutical may be used as a pharmaceutical for prevention or treatment of a disease that can be prevented or treated by ingestion or administration of the functional substance. The formulation of the pharmaceutical may be selected in accordance with the disease to be prevented or treated, the mode of use of the pharmaceutical, the administration route, and/or the like. Examples of the formulation include tablets, coated tablets, balls, capsules, granules, powders, solutions, suspensions, emulsions, syrups, injection solutions, suppositories, infusions, decoctions, and tinctures. These preparations may be prepared according to conventional methods using, when necessary, known adjuvants that can be normally used in the technical field of preparation of pharmaceuticals, such as fillers, bulking agents, excipients, binders, moisturizing agents, disintegrators, surfactants, lubricants, coloring agents, correctives, solubilizers, suspending agents, and coating agents, in addition to the principal component. The pharmaceutical may also contain a coloring agent, preservative, perfume, flavoring agent, sweetener, or other pharmaceuticals.

The content of the functional substance produced in the step described above with respect to the total amount of the pharmaceutical is not limited. The content is preferably a content with which a desired effect can be obtained from the functional substance when the pharmaceutical is ingested or administered. The content of the functional substance with respect to the total amount of the pharmaceutical is dependent on the type and the desired effect of the functional substance, and may be selected within the range of usually 0.001 wt % to 80 wt %, preferably 0.01 wt % to 50 wt %, more preferably 0.1 wt % to 25 wt %.

Another aspect of the present invention is a method for producing a quasi-drug.

The method for producing a quasi-drug of the present aspect comprises the step of producing a functional substance utilizing a reaction requiring hydrogen, the hydrogen being supplied by culturing of a hydrogen-producing microorganism. Regarding details of the method, the description for the method for producing a functional substance is applied.

The method for producing a quasi-drug of the present aspect also comprises the step of mixing the functional substance with a raw material of a quasi-drug. Regarding details of the method, the description for the method for producing a pharmaceutical is applied.

EXAMPLES

The present invention is described below in more detail by way of specific examples. However, the present invention is not limited to these examples.

<1. Method for Producing Urolithin Compounds>
(Preparation of Preculture Medium)

To Anaerobe Basal Broth (ABB) medium, manufactured by Thermo Scientific, ellagic acid was added to 0.1 g/L, and 10 mL of the resulting mixture was dispensed into a test tube. Gas replacement was carried out with nitrogen gas followed by sterilization.

(Preparation of Main Culture Medium)

Ellagic acid was added to ABB medium, and 10 mL of the resulting mixture was dispensed into a test tube. Gas replacement was carried out with nitrogen gas followed by sterilization.

(Preculture)

The microorganisms in each combination shown in Table 1 were inoculated into the preculture medium. Thereafter, gas replacement was carried out with nitrogen gas, and then culture was performed at 37° C. at 200 spm for 2 days.

As a microorganism which produces a urolithin compound from ellagic acid, but which does not substantially produce hydrogen, one of the *Gordonibacter pamelaeae* DSM 19378 strain, *Gordonibacter urolithinfaciens* DSM 27213 strain, *Gordonibacter faecihominis* JCM 16058 strain, and *Eggerthella* sp. DC3563 (NITE BP-02376) strain was used.

As a hydrogen-producing microorganism, one of the *Clostridium asparagiforme* DSM 15981 strain, *Clostridium bolteae* JCM 12243 strain, and *Clostridium citroniae* DSM 19261 strain was used.

(Main Culture)

The microorganisms after the preculture were inoculated into the main culture medium, and gas replacement was carried out with nitrogen gas, followed by performing culture at 37° C. at 200 spm for 3 days.

(Method for Measuring Yields of Urolithin Compounds)

To 1 mL of the culture liquid after the main culture, 10 µL of formic acid and 1 mL of DMSO were added, and the resulting mixture was vortexed. After performing centrifugation at 3000 rpm for 10 minutes, filtration was carried out through a PVDF membrane with a pore size of 0.45 μm. The filtrate was diluted 10-fold with sterile water, and then analyzed under the following HPLC conditions.

<HPLC Conditions>
  Column: Inertsil ODS-3 (4.6 mm (diameter)×250 mm, 5 μm) (GL Sciences)
  Eluent: Solution A, $H_2O$/HCOOH=99:1 (v/v); Solution B, $CH_3CN$/HCOOH=99:1 (v/v)
  Gradient: (A)/(B)=80/20 (10 min)→5 min→10/90 (5 min)→80/20 (10 min)
  Temperature: 40° C.
  Detection: PDA (305 nm)
  Flow rate: 1.0 mL/min
  Injection: 10 μL
  Time: 30 min (Results)
The results are shown in Table 1.

TABLE 1

| | *1 | *2 | Gas phase | Ellagic acid | \multicolumn{6}{c}{Yields of urolithin compounds (%)} |
|---|---|---|---|---|---|---|---|---|---|---|
| | | | | | M6 | D | E | C | M7 | A |
| Comparative Example 1-1 | GP | — | $N_2$ | 12.5 | 0.1 | 0.0 | 0.1 | 0.1 | 0.0 | 0.0 |
| Comparative Example 1-2 | GP | — | $H_2$ | 13.1 | 3.7 | 0.3 | 0.1 | 20.3 | 0.0 | 0.0 |
| Example 1-1 | GP | CA | $N_2$ | 3.8 | 0.0 | 0.0 | 0.0 | 1.2 | 0.0 | 105.0 |
| Example 1-2 | GP | CB | $N_2$ | 1.8 | 0.0 | 0.0 | 0.5 | 0.2 | 13.3 | 51.2 |
| Example 1-3 | GP | CC | $N_2$ | 8.2 | 0.0 | 0.0 | 0.4 | 1.0 | 1.3 | 76.2 |
| Comparative Example 2-1 | GU | — | $N_2$ | 7.1 | 0.0 | 0.1 | 0.0 | 0.0 | 0.0 | 0.0 |
| Comparative Example 2-2 | GU | — | $H_2$ | 6.7 | 0.5 | 0.0 | 6.7 | 0.2 | 0.0 | 0.0 |
| Example 2-1 | GU | CA | $N_2$ | 14.9 | 0.0 | 0.0 | 0.4 | 4.7 | 6.7 | 32.2 |
| Example 2-2 | GU | CB | $N_2$ | 12.0 | 0.0 | 0.2 | 7.1 | 0.4 | 18.0 | 7.5 |
| Example 2-3 | GU | CC | $N_2$ | 16.5 | 0.0 | 0.1 | 6.9 | 4.5 | 0.8 | 9.8 |
| Comparative Example 3-1 | Esp | — | $N_2$ | 80.3 | 0.0 | 0.0 | 0.0 | 0.0 | 0.0 | 0.0 |
| Comparative Example 3-2 | Esp | — | $H_2$ | 94.4 | 0.0 | 0.0 | 0.0 | 25.1 | 0.0 | 0.0 |
| Example 3-1 | Esp | CA | $N_2$ | 1.1 | 0.0 | 0.0 | 0.2 | 0.7 | 0.0 | 112.0 |
| Example 3-2 | Esp | CB | $N_2$ | 1.2 | 0.0 | 0.0 | 0.6 | 0.4 | 8.4 | 81.9 |
| Example 3-3 | Esp | CC | $N_2$ | 10.4 | 0.0 | 0.0 | 0.5 | 1.7 | 0.0 | 69.4 |
| Comparative Example 4-1 | GF | — | $N_2$ | 10.5 | 0.1 | 0 | 0 | 0.1 | 0 | 0 |
| Comparative Example 4-2 | GF | — | $H_2$ | 9.8 | 16.3 | 0 | 0 | 3.2 | 0 | 0 |
| Example 4-1 | GF | CA | $N_2$ | 2.3 | 0 | 0 | 0 | 1.3 | 0 | 83.8 |
| Example 4-2 | GF | CB | $N_2$ | 13.1 | 0 | 0 | 16.7 | 0.2 | 29.4 | 7.5 |
| Example 4-3 | GF | CC | $N_2$ | 11.7 | 0 | 0 | 1.5 | 9.2 | 0 | 56.1 |

*1: Microorganism which produces functional substance; *2: Hydrogen-producing microorganism The names of the microorganisms in Table 1 are as described below.
  GP: *Gordonibacter pamelaeae* DSM 19378 strain
  GU: *Gordonibacter urolithinfaciens* DSM 27213 strain
  Esp: *Eggerthella* sp. DC3563 (NITE BP-02376) strain
  GF: *Gordonibacter faecihominis* JCM 16058 strain
  CA: *Clostridium asparagiforme* DSM 15981 strain
  CB: *Clostridium bolteae* JCM 12243 strain
  CC: *Clostridium citroniae* DSM 19261 strain First, results of Comparative Examples revealed that, regarding urolithin C, when no hydrogen-producing microorganism is present, production of urolithin C is higher in cases where the gas phase is hydrogen gas than in cases where the gas phase is nitrogen gas.

Subsequently, it was revealed that the presence of a hydrogen-producing microorganism increases production of urolithin A.

Here, each microorganism which produces a functional substance is a microorganism which produces urolithin C from ellagic acid, but which does not produce urolithin A from urolithin C.

Each hydrogen-producing microorganism is a microorganism which produces neither urolithin C nor urolithin A from ellagic acid, but which produces urolithin A from urolithin C.

Thus, the urolithin A produced is thought to have been produced from urolithin C by the hydrogen-producing microorganism. The urolithin C is thought to have been produced from ellagic acid by each microorganism that produces a functional substance, and the hydrogen for this process is thought to have been supplied from each hydrogen-producing microorganism.

Production of urolithin A from urolithin C by the *Clostridium asparagiforme* DSM 15981 strain, *Clostridium bolteae* JCM 12243 strain, and *Clostridium citroniae* DSM 19261 strain was demonstrated by the following Reference Examples 1 to 3.

Reference Example 1

Urolithin C was added to ABB medium (manufactured by Oxoid Limited) and then heat-sterilized, followed by replacing the gas phase with $N_2$:$CO_2$:$H_2$ (80%/10%/10%) gas to provide a basal medium. To the basal medium, which contains urolithin C at a final concentration of 1.0 g/L, the *Clostridium asparagiforme* DSM 15981 strain was inoculated, and culture was carried out anaerobically at 37° C. After completion of the culture, 5 mL of ethyl acetate was added to the same amount of the culture liquid to extract urolithin compounds, and the resulting ethyl acetate phase was concentrated under reduced pressure to dryness. The thus obtained dried product was redissolved in 0.5 mL of methanol, and quantitative analysis of urolithin compounds was carried out by HPLC.

The HPLC was carried out under the later-described conditions. Urolithin compounds manufactured by DALTON PHARMA, after dissolution in DMSO, were used as standard samples. As a result of 5 weeks of the culture, 95% of the urolithin C added was converted to urolithin A.

Reference Example 2

The same operation as in Reference Example 1 was carried out except that 2 weeks of culture was performed using the *Clostridium bolteae* JCM 12243 strain as the microorganism.

As a result, 89% of the urolithin C added was converted to urolithin A.

Reference Example 3

The same operation as in Reference Example 1 was carried out except that 5 days of culture was performed using the *Clostridium citroniae* DSM 19261 strain as the microorganism.

As a result, 82% of the urolithin C added was converted to urolithin A.

<HPLC Conditions>
Column: Inertsil ODS-3 (250×4.6 mm) (manufactured by GL Science)
Eluent: water/acetonitrile/acetic acid=74/25/1
Flow rate: 1.0 mL/min
Column temperature: 40° C.
Detection: 305 nm <2. Method for Producing Equol: Part 1>
(Preparation of Preculture Medium)

Into a test tube, 10 mL of Anaerobe Basal Broth (ABB) medium, manufactured by Thermo Scientific, was dispensed. Gas replacement was carried out with nitrogen gas followed by sterilization.

(Preparation of Main Culture Medium)

Daidzein was added to ABB medium, and 10 mL of the resulting mixture was dispensed into a test tube. Gas replacement was carried out with nitrogen gas followed by sterilization.

(Preculture)

The microorganisms in each combination shown in Table 2 were inoculated into the preculture medium. Thereafter, gas replacement was carried out with nitrogen gas, and then culture was performed for 2 days.

As a microorganism which produces equol from daidzein, but which does not substantially produce hydrogen, one of the *Asaccharobacter celatus* DSM 18785 strain and *Adlercreutzia equolifaciens* DSM 19450 strain was used.

As a hydrogen-producing microorganism, one of the *Clostridium asparagiforme* DSM 15981 strain, *Clostridium bolteae* JCM 12243 strain, and *Clostridium citroniae* DSM 19261 strain was used.

(Main Culture)

The microorganisms after the preculture were inoculated into the main culture medium, and gas replacement was carried out with nitrogen gas, followed by performing culture at 37° C. at 200 spm for 3 days.

(Method for Measuring Equol)

After the main culture, 20 μL of the culture liquid was sampled, and then diluted 50-fold with a dilution liquid (ethanol: Milli-Q water=70:30 (v/v)). After filtration through a 0.45-μm filter, the supernatant was analyzed under the following HPLC conditions.

<HPLC Conditions>
Column: Phenomenex SYNERGI, 4 μm, POLAR-R, 150 mm×4.6 mm
Eluent: distilled water/methanol=55/45 (v/v)
Temperature: 40° C.
Detection: 280 nm
Flow rate: 1.0 mL/min
Injection: 10 μL
Time: 30 min (Results)

The results are shown in Table 2. From Table 2, production of equol from daidzein could be confirmed.

TABLE 2

| | Microorganism which produces equol | Hydrogen-producing microorganism | Gas phase | Equol yield (%) |
|---|---|---|---|---|
| Example 5-1 | AC | CA | $N_2$ | 79 |
| Example 5-2 | AC | CB | $N_2$ | 27 |
| Example 5-3 | AC | CC | $N_2$ | 78 |
| Example 6-1 | AE | CA | $N_2$ | 76 |
| Example 6-2 | AE | CB | $N_2$ | 12 |
| Example 6-3 | AE | CC | $N_2$ | 75 |

The names of the microorganisms in Table 2 are as described below.

AC: *Asaccharobacter celatus* DSM 18785 strain
AE: *Adlercreutzia equolifaciens* DSM 19450 strain
CA: *Clostridium asparagiforme* DSM 15981 strain
CB: *Clostridium bolteae* JCM 12243 strain
CC: *Clostridium citroniae* DSM 19261 strain (Influence of Hydrogen Gas)

Using the *Asaccharobacter celatus* DSM 18785 strain as a microorganism which produces equol from daidzein, but which does not substantially produce hydrogen, the same operation as in Example 5-1 was carried out except that no hydrogen-producing microorganism was used, and that the gas phase described in Table 3 was used.

(Results)

The results are shown in Table 3. From Table 3, contribution of hydrogen gas to improved production of equol can be seen.

Thus, it is thought that, in Example 5-1 to Example 5-3, and Example 6-1 to Example 6-3, the microorganism which produces equol used hydrogen supplied from the hydrogen-producing microorganism, to produce the equol.

TABLE 3

| | Microorganism which produces equol | $H_2$ (%) | $N_2$ (%) | $CO_2$ (%) | Equol concentration (μM) |
|---|---|---|---|---|---|
| Example 7-1 | AC | 20 | 0 | 80 | 320 |
| Example 7-2 | AC | 0 | 0 | 100 | 10 |
| Example 7-3 | AC | 0 | 100 | 0 | 9 |

<3. Method for Producing Equol: Part 2>
(Preparation of Preculture Medium)

50 mL of Anaerobe Basal Broth (ABB) medium, manufactured by Thermo Scientific, was dispensed. Gas replacement was carried out with nitrogen gas followed by sterilization.

(Preparation of Main Culture Medium)

Daidzein was added to ABB medium, and the resulting mixture was dispensed into a jar fermenter. Gas replacement was carried out with nitrogen gas followed by sterilization.

(Preculture)

The microorganisms in each combination shown in Table 4 were inoculated into the preculture medium. Thereafter, gas replacement was carried out with nitrogen gas, and then culture was performed at 37° C. at 200 spm.

As a microorganism which produces equol from daidzein, but which does not substantially produce hydrogen, the *Asaccharobacter celatus* DSM 18785 strain was used.

As a hydrogen-producing microorganism, the *Clostridium asparagiforme* DSM 15981 strain was used.

(Main Culture)

The microorganisms after the preculture were inoculated into the main culture medium, and gas replacement was carried out with nitrogen gas, followed by performing culture for 5 days with stirring at various stirring rates.

(Method for Measuring Equol)

After the main culture, 20 μL of the culture liquid was sampled, and then diluted 50-fold with a dilution liquid (ethanol: Milli-Q water=70:30 (v/v)). After filtration through a 0.45-μm filter, the supernatant was analyzed under the following HPLC conditions.

<HPLC Conditions>
  Column: Phenomenex SYNERGI, 4 μm, POLAR-R, 150 mm×4.6 mm
  Eluent: distilled water/methanol=55/45 (v/v)
  Temperature: 40° C.
  Detection: 280 nm
  Flow rate: 1.0 mL/min
  Injection: 10 μL
  Time: 30 min (Results)

The results are shown in Table 4. From the results of Reference Example 4, Example 8-1, and Example 8-2, it was found that, in cases where the gas phase is not hydrogen, but where a hydrogen-producing microorganism is present, an equivalent equol yield can be obtained at a lower stirring rate compared to cases where the gas phase is hydrogen, but where no hydrogen-producing microorganism is present.

Further, from the results of Reference Example 5 and Example 8-1, it was found that the equol yield at the same stirring rate is much higher in cases where the gas phase is not hydrogen, but where a hydrogen-producing microorganism is present, compared to cases where the gas phase is hydrogen, but where no hydrogen-producing microorganism is present.

TABLE 4

| | Microorganism which produces equol | Hydrogen-producing microorganism | Gas phase | Stirring rate (rpm) | Equol yield (%) |
|---|---|---|---|---|---|
| Reference Example 4 | AC | None | $H_2$ | 500 | 83 |
| Reference Example 5 | AC | None | $H_2$ | 300 | 47 |
| Example 8-1 | AC | CA | $N_2$ | 300 | 85 |
| Example 8-2 | AC | CA | $N_2$ | 200 | 85 |

The names of the microorganisms in Table 4 are as described below.

AC: *Asaccharobacter celatus* DSM 18785 strain
CA: *Clostridium asparagiforme* DSM 15981 strain

What is claimed is:

1. A method for producing a functional substance utilizing a reaction requiring hydrogen, the method comprising:
   supplying the hydrogen, wherein the hydrogen is produced by culturing of a hydrogen-producing microorganism, wherein the hydrogen-producing microorganism is one or more bacteria belonging to *Clostridium asparagiforme*, *Clostridium bolteae*, or *Clostridium citroniae*; and
   culturing a microorganism which produces the functional substance with the supplied hydrogen, wherein the microorganism which produces the functional substance is one or more bacteria belonging to *Asaccharobacter celatus* or *Adlercreutzia equolifaciens*;
   wherein the functional substance comprises an equol compound,
   wherein the culturing of the microorganism which produces the functional substance is performed in culture media comprising daidzein, and
   wherein the equol compound is produced from daidzein present in the culture media.

2. The method according to claim 1, wherein the equol compound is equol or 5-hydroxyequol.

3. A method for producing a functional food, the method comprising:
   producing a functional substance utilizing a reaction requiring hydrogen, the hydrogen being supplied from a hydrogen-producing microorganism in culture, wherein the hydrogen-producing microorganism is one or more bacteria belonging to *Clostridium asparagiforme*, *Clostridium bolteae*, or *Clostridium citroniae*;
   culturing a microorganism which produces the functional substance with the supplied hydrogen, wherein the microorganism which produces the functional substance is one or more bacteria belonging to *Asaccharobacter celatus* or *Adlercreutzia equolifaciens*; and
   mixing the functional substance with a raw material of a food,
   wherein the microorganism which produces the functional substance utilizes the hydrogen supplied from the hydrogen-producing microorganism to produce the functional substance, and
   wherein the functional substance comprises an equol compound,
   wherein the culturing of the microorganism which produces the functional substance is performed in culture media comprising daidzein, and
   wherein the equol compound is produced from daidzein present in the culture media.

4. The method according to claim 3, wherein the equol compound is equol or 5-hydroxyequol.

5. A method for producing an equol compound utilizing a reaction requiring hydrogen, the method comprising:
   supplying the hydrogen by culturing of a hydrogen-producing microorganism; and
   co-culturing a microorganism which produces the equol compound with the hydrogen-producing microorganism,
   wherein the microorganism which produces the equol compound utilizes the hydrogen supplied from the hydrogen-producing microorganism to produce the equol compound,
   wherein the hydrogen-producing microorganism is one or more bacteria belonging to *Clostridium asparagiforme*, *Clostridium bolteae*, or *Clostridium citroniae*, and
   wherein the microorganism which produces the equol compound is one or more bacteria belonging to *Asaccharobacter celatus* or *Adlercreutzia equolifaciens*,
   wherein the co-culturing is performed in culture media comprising daidzein, and
   wherein the equol compound is produced from daidzein present in the culture media.

6. The method according to claim 5, wherein the equol compound is equol or 5-hydroxyequol.

7. A method for producing a functional food, the method comprising:
   co-culturing a microorganism which produces a functional substance with a hydrogen-producing microorganism, wherein the microorganism which produces the functional substance is one or more bacteria belonging to *Asaccharobacter celatus* or *Adlercreutzia eguolifaciens*;

producing the functional substance utilizing a reaction requiring hydrogen, the hydrogen supplied by the hydrogen-producing microorganism, wherein the functional substance comprises an equol compound; and mixing the functional substance with a raw material of a food, wherein the hydrogen-producing microorganism is one or more bacteria belonging to *Clostridium asparagiforme*, *Clostridium bolteae*, or *Clostridium citroniae*, wherein the co-culturing is performed in culture media comprising daidzein, and wherein the equol compound is produced from daidzein present in the culture media.

8. The method according to claim 7, wherein the equol compound is equol or 5-hydroxyequol.

* * * * *